United States Patent
Narasimha-Iyer et al.

(10) Patent No.: US 9,241,626 B2
(45) Date of Patent: Jan. 26, 2016

(54) SYSTEMS AND METHODS FOR IMPROVED ACQUISITION OF OPHTHALMIC OPTICAL COHERENCE TOMOGRAPHY DATA

(71) Applicant: Carl Zeiss Meditec, Inc., Dublin, CA (US)

(72) Inventors: Harihar Narasimha-Iyer, Livermore, CA (US); Tilman Schmoll, Dublin, CA (US); Utkarsh Sharma, Dublin, CA (US); Siddharth Srivastava, Hayward, CA (US); Alexandre R. Tumlinson, San Leandro, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 51 days.

(21) Appl. No.: 14/199,847

(22) Filed: Mar. 6, 2014

(65) Prior Publication Data
US 2014/0268046 A1    Sep. 18, 2014

Related U.S. Application Data

(60) Provisional application No. 61/785,420, filed on Mar. 14, 2013.

(51) Int. Cl.
| | |
|---|---|
| A61B 3/14 | (2006.01) |
| A61B 3/00 | (2006.01) |
| A61B 3/10 | (2006.01) |
| G06T 5/50 | (2006.01) |
| G06T 5/00 | (2006.01) |

(52) U.S. Cl.
CPC .................. *A61B 3/102* (2013.01); *G06T 5/002* (2013.01); *G06T 5/50* (2013.01); *G06T 2207/10101* (2013.01); *G06T 2207/30041* (2013.01); *G06T 2207/30168* (2013.01)

(58) Field of Classification Search
USPC .................................................. 351/200–246
See application file for complete search history.

(56) References Cited

U.S. PATENT DOCUMENTS

| | | | |
|---|---|---|---|
| 5,321,501 | A  | 6/1994  | Swanson et al. |
| 5,537,162 | A  | 7/1996  | Hellmuth et al. |
| 7,301,644 | B2 | 11/2007 | Knighton et al. |
| 7,884,945 | B2 | 2/2011  | Srinivasan et al. |
| 8,401,257 | B2 | 3/2013  | Izatt et al. |

(Continued)

OTHER PUBLICATIONS

Atchison et al., "Eye Shape in Emmetropia and Myopia", Investigative Ophthalmology & Visual Science, vol. 45, No. 10, Oct. 2004, pp. 3380-3386.

(Continued)

*Primary Examiner* — Mohammed Hasan
(74) *Attorney, Agent, or Firm* — Morrison & Foerster LLP

(57) ABSTRACT

Systems and methods for improved acquisition of ophthalmic optical coherence tomography data are presented, allowing for enhanced ease of use and higher quality data and analysis functionality. Embodiments include automated triggering for detecting and initiating collection of OCT ophthalmic data, an automated technique for determining the optimal number of B-scans to be collected to create the highest quality image and optimize speckle reduction, automated review of fundus images collected with an adjunct imaging modality to guide the OCT data collection, a single scan protocol in which a large field of view is collected with HD B-scans embedded at different locations depending on automated analysis of either a fundus image or sparse OCT scan, and various scan configurations for imaging eyes with large axial depth range.

20 Claims, 4 Drawing Sheets

(56) References Cited

U.S. PATENT DOCUMENTS

| | | | |
|---|---|---|---|
| 2007/0291277 A1 | 12/2007 | Everett et al. | |
| 2009/0268162 A1* | 10/2009 | Stetson et al. | 351/246 |
| 2011/0170062 A1 | 7/2011 | Isogai et al. | |
| 2012/0127438 A1 | 5/2012 | Shimizu et al. | |
| 2012/0249956 A1 | 10/2012 | Narasimha-Iyer et al. | |
| 2013/0120757 A1 | 5/2013 | Yu et al. | |
| 2013/0188140 A1* | 7/2013 | Bagherinia et al. | 351/206 |
| 2013/0208240 A1* | 8/2013 | Sharma et al. | 351/206 |

OTHER PUBLICATIONS

Choma et al., "Sensitivity Advantage of Swept Source and Fourier Domain Optical Coherence Tomography", Optics Express, vol. 11, No. 18, Sep. 8, 2003, pp. 2183-2189.

Huang et al., "Optical Coherence Tomography", Science, vol. 254, Nov. 22, 1991, pp. 1178-1181.

Lee et al., "In vivo Optical Frequency Domain Imaging of Human Retina and Choroid", Optics Express, vol. 14, No. 10, May 15, 2006, pp. 4403-4411.

Leitgeb et al., "Ultrahigh Resolution Fourier Domain Optical Coherence Tomography", Optics Express, vol. 12, No. 10, May 17, 2004, pp. 2156-2165.

Narasimha-Iyer et al., "Integrated Analysis of Vascular and Non-Vascular Changes from Color Retinal Fundus Image Sequences", IEEE Transactions on Biomedical Engineering, Aug. 2007, pp. 1-33.

Narasimha-Iyer et al., "Robust Detection and Classification of Longitudinal Changes in Color Retinal Fundus Images for Monitoring Diabetic Retinopathy", IEEE Transactions of Biomedical Engineering, vol. 53, No. 6, Jun. 2006, pp. 1-15.

Nassif et al., "In vivo Human Retinal Imaging by Ultrahigh-Speed Spectral Domain Optical Coherence Tomography", Optics Letters, vol. 29, No. 5, Mar. 1, 2004, pp. 480-482.

Optos, "Achieving the Vision: Delivering 'The Ultimate Diagnostics machine'", Optos Ultra-wide Field Fundus Advert, Jul. 2012, 1 page.

Wojtkowski et al., "Three-dimensional Retinal Imaging with High-Speed Ultrahigh-Resolution Optical Coherence Tomography", Ophthalmology, vol. 112, No. 10, Oct. 2005, pp. 1734-1746.

* cited by examiner

| Degrees scan | Emmetropia | High Myopia |
|---|---|---|
| 0 | 0 | 0 |
| 10 | -0.1 | -0.5 |
| 20 | -0.6 | -2.2 |
| 30 | -1.3 | -4.9 |

SYSTEMS AND METHODS FOR IMPROVED ACQUISITION OF OPHTHALMIC OPTICAL COHERENCE TOMOGRAPHY DATA

PRIORITY

The present application claims priority to U.S. Provisional Application Ser. No. 61/785,420 filed Mar. 14, 2013 hereby incorporated in its entirety by reference.

TECHNICAL FIELD

The present invention relates to optical imaging, and in particular to improvements in acquisition of ophthalmic optical coherence tomography imaging data.

BACKGROUND

Optical Coherence Tomography (OCT) is a technique for performing high-resolution cross-sectional imaging that can provide images of tissue structure on the micron scale in situ and in real time (Huang et al. "Optical Coherence Tomography" Science 254(5035):1178 1991). OCT is a method of interferometry that determines the scattering profile of a sample along the OCT beam. Each scattering profile is called an axial scan, or A-scan. Cross-sectional images (B-scans), and by extension 3D volumes, are built up from many A-scans, with the OCT beam moved to a set of transverse locations on the sample. OCT provides a mechanism for micrometer resolution measurements.

In frequency domain OCT (FD-OCT), the interferometric signal between light from a reference and the back-scattered light from a sample point is recorded in the frequency domain rather than the time domain. After a wavelength calibration, a one-dimensional Fourier transform is taken to obtain an A-line spatial distribution of the object scattering potential. The spectral information discrimination in FD-OCT is typically accomplished by using a dispersive spectrometer in the detection arm in the case of spectral-domain OCT (SD-OCT) or rapidly scanning a swept laser source in the case of swept-source OCT (SS-OCT).

Evaluation of biological materials using OCT was first disclosed in the early 1990's (see for example U.S. Pat. No. 5,321,501). Frequency domain OCT techniques have been applied to living samples (see for example Nassif et al. "In vivo human retinal imaging by ultrahigh-speed spectral domain optical coherence tomography" Optics Letters 29(5): 480 2004). The frequency domain techniques have significant advantages in speed and signal-to-noise ratio as compared to time domain OCT (see for example Choma, M. A., et al. "Sensitivity advantage of swept source and Fourier domain optical coherence tomography" Optics Express 11(18): 2183 2003). The greater speed of modern OCT systems allows the acquisition of larger data sets, including 3D volume images of human tissue. OCT has found widespread use in the field of ophthalmology as evidenced by numerous commercially available ophthalmic OCT devices including the Stratus, Cirrus HD-OCT, and Visante (Carl Zeiss Meditec, Inc. Dublin, Calif.). Technology development in the field continues with efforts towards increasing the ease of use of the instruments, improving analytic functionality and increasing reliability of data when imaging patients with various abnormalities.

SUMMARY

Aspects of the present invention are directed towards improvements in acquisition of ophthalmic optical coherence tomography data, allowing for enhanced ease of use and higher quality data and analysis functionality. In one embodiment of the present invention, an automated start trigger is described for detecting and initiating collection of OCT ophthalmic data. In a second embodiment, an automated technique for determining the optimal number of B-scans to be collected to create the highest quality image and optimize speckle reduction is presented. Another embodiment of the invention is directed towards automated review of fundus images collected with an adjunct imaging modality to guide the OCT data collection. In a further embodiment of the invention, a single scan protocol is described in which a large field of view is collected with HD B-scans embedded at different locations depending on automated analysis of either a fundus image or sparse OCT scan. In a final embodiment of the invention various scan configurations for imaging eyes with large axial depth range.

BRIEF DESCRIPTION OF THE FIGURES

FIG. 5(a) illustrates equatorial stretching, FIG. 5(b) illustrates posterior pole elongation, and FIG. 5(c) illustrates global expansion

FIG. 7 illustrates two scanning approaches that can be taken to image highly myopic eyes.

DETAILED DESCRIPTION

Figure 1:
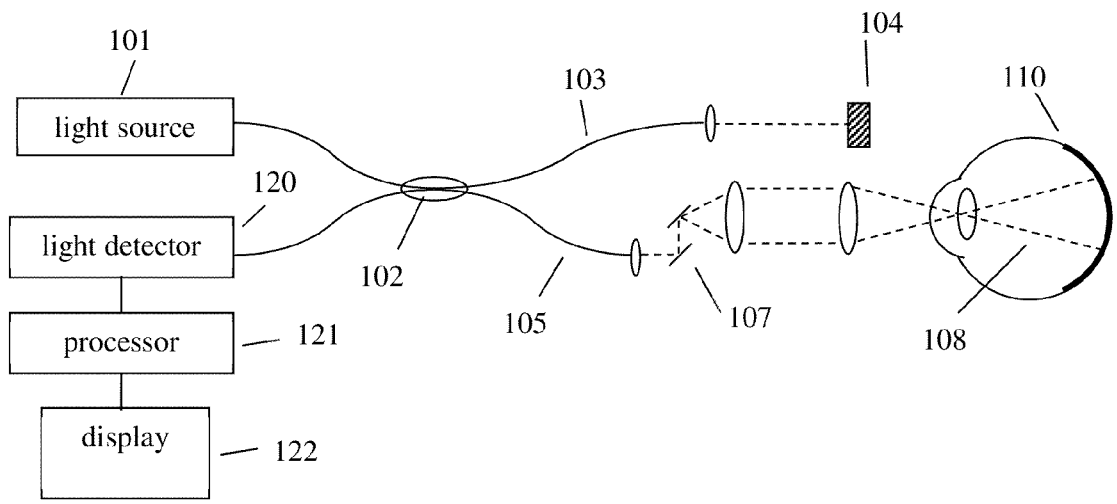
FIG. 1 illustrates a generalized ophthalmic OCT system that could be used in the various embodiments of the present invention.

A generalized FD-OCT system used to collect 3-D image data suitable for use with the present invention is illustrated in FIG. 1. A FD-OCT system includes a light source, 101, typical sources including but not limited to broadband light sources with short temporal coherence lengths or swept laser sources. (See for example, Wojtkowski, et al., "Three-dimensional retinal imaging with high-speed ultrahigh-resolution optical coherence tomography," *Ophthalmology* 112(10):1734 2005 or Lee et al. "In vivo optical frequency domain imaging of human retina and choroid," *Optics Express* 14(10):4403 2006)

Light from source 101 is routed, typically by optical fiber 105, to illuminate the sample 110, a typical sample being tissues at the back of the human eye. The light is scanned, typically with a scanner 107 between the output of the fiber and the sample, so that the beam of light (dashed line 108) is scanned over the area or volume to be imaged. Light scattered from the sample is collected, typically into the same fiber 105 used to route the light for illumination. Reference light derived from the same source 101 travels a separate path, in this case involving fiber 103 and retro-reflector 104. Those skilled in the art recognize that a transmissive reference path can also be used. Collected sample light is combined with reference light, typically in a fiber coupler 102, to form light interference in a detector 120. The output from the detector is supplied to a processor 130. The results can be stored in the processor or displayed on display 140. The processing and storing functions may be localized within the OCT instrument or functions may be performed on an external processing unit to which the collected data is transferred. This unit could be dedicated to data processing or perform other tasks which are quite general and not dedicated to the OCT device.

The interference causes the intensity of the interfered light to vary across the spectrum. The Fourier transform of the interference light reveals the profile of scattering intensities at different path lengths, and therefore scattering as a function of depth (z-direction) in the sample (see for example Leitgeb et al. "Ultrahigh resolution Fourier domain optical coherence tomography," Optics Express 12(10):2156 (2004)). The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are typically used at the detection port for SD-OCT systems. The invention described herein could be applied to any type of OCT system. In various embodiments of the present invention, a secondary imaging modality can be included with the OCT system.

Start Trigger for Ophthalmic OCT Acquisition

OCT instrument operators often ask the patient to blink once or twice before they start acquisition of data. Often times, however, the operator does not immediately recognize the blinking or take an unnecessarily long time to determine if the image quality and alignment is as good as before the blinking. This increases the time between blinking and start of acquisition and leaves less time before the patient is likely to blink or move again. Therefore the patient is more likely to blink or move again during the acquisition. In one aspect of the present invention, the system automatically detects blinking of the patient, and starts the acquisition automatically, minimizing the time during which the patient has to stare into the device without blinking.

In order to reduce the often unnecessarily long time between blinking of the patient and start of the OCT acquisition, the device would detect for example the double blink of the patient, and then automatically start acquiring data. Since blinking blocks the light going into the eye and therefore directly results in OCT signal loss from e.g. the retina, the blinking is easily detectable using optical techniques by looking for a strong instantaneous decrease or increase in optical signal. This could be accomplished using unprocessed or processed OCT data. One example would be to analyze the intensity of a series of fundus images generated from the OCT data in real time using a technique as described in U.S. Pat. No. 7,301,644 hereby incorporated by reference. Alternatively, a stream of images from an adjunct camera like an Iris Viewer as described in US Patent Publication No. 2007/0291277 hereby incorporated by reference, could be analyzed to detect when the eye is closed while blinking. In order to assure that the alignment is maintained after the blinking, the device may correlate the scans before and after the blinking. If sufficient correlation is achieved, the device may automatically start the acquisition. Such an automatic start of image acquisition would reduce the time the patient has to try not to blink and therefore ultimately improves patient comfort.

Automated Variable HD Averaging for Optimal Scan Collection

Averaging multiple B-Scans is a method to reduce the speckle in the image and to improve the quality leading to what are commonly referred to as high definition (HD) scans. In addition to averaging, high definition scans can also be collected with a denser sampling and hence a higher resolution. The quality of the averaged B-Scan first improves with the number of lines being averaged. However, there is a plateau and further averaging does not increase the quality greatly. Currently, commercially available OCT systems only give a pre-determined number for the averaging or allow the user to set the number of lines to be averaged before the start of acquisition. However, even when there is flexibility in selecting the number of lines, the user has to set the number to a high number to ensure that they get the best quality possible. However as described earlier, the improvement in quality with the number of lines that are averaged drops down significantly after a few lines. This break-point might be different for different eyes depending on the pathology, media condition, imaging condition etc.

In a further aspect of the present invention, the OCT system automatically determines and evaluates a quality metric during the acquisition of multiple scans and uses this metric to determine the optimal number of scans to be acquired and used to generate an image. In a preferred embodiment, a metric is developed based on the image quality of an averaged B-scan, wherein after an initial subset are collected, the impact on the quality metric by averaging additional scans is assessed. In this way, the instrument provides real time feedback on the data quality that can drive further acquisition, thus saving user time (by not acquiring unnecessary data to be averaged) as well as guaranteeing that the best final images are provided to the user. The system can automatically find this optimal number of B-Scans to be averaged and to drive the acquisition based on this number. Hence the user will not have to preset the number of B-Scans to be averaged and is ensured that he gets the best quality of images possible. In a preferred embodiment of the present invention, the system includes a tracking system such as is described in US Patent Publication No. 2012/0249956 that enables the collection of any number of B-Scans at the same location.

Figure 2:
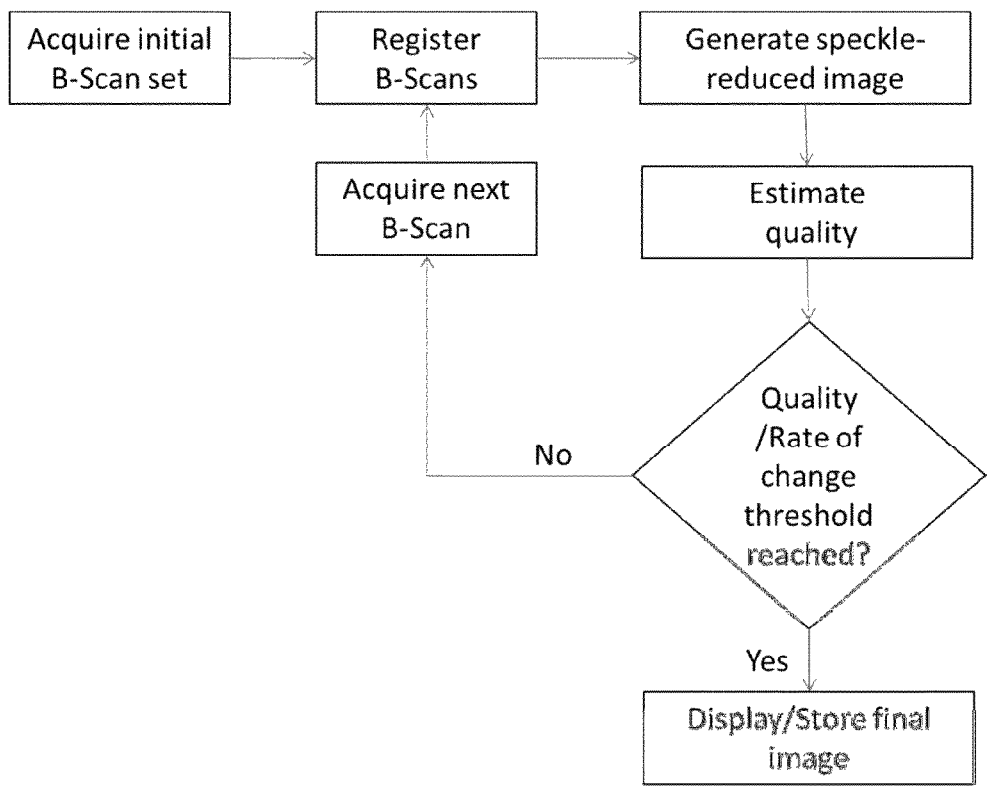
FIG. 2 shows a flow chart of the basic steps in an embodiment of the present invention directed towards optimizing collection of the number of B-scans to be used to generate a high definition averaged B-scan.

The steps in the preferred approach are given in FIG. 2. An initial set of B-Scans is first acquired and averaged (This number can be a small number such as 4-10) where it is known that there is a definite improvement in image quality with the number of B-Scans being averaged. As previously mentioned, it is desirable that these B-scans be acquired with a system capable of tracking the placement of the scans to ensure the data is collected at the same transverse locations. Alternatively the data could be registered in post-processing as will be discussed in further detail below. This number could also be as low as two if we want the system to be fully adaptive.

Once the initial set of B-Scans is averaged and a speckle-reduced B-Scan is generated, a quality metric is calculated on this image. Quality metrics looking at the overall intensity characteristics of the image could be devised or metrics corresponding to particular layers/regions (for example the RPE or the ELM) could be evaluated. Those skilled in the art could also imagine quality metrics that combine different intensity characteristics such as brightness and contrast. Smoothness characteristics, as well as metrics derived from layer/region segmentations can also be envisioned.

The next step is to compare this quality value with an absolute threshold or look at relative changes in this quality metric based on successive B-Scans that are added to the average. If an absolute quality threshold is met or if the improvement is below a certain threshold, then the acquisition engine can be instructed to stop acquiring images for this B-Scan and proceed to the next location to be imaged. If the thresholds are not met, then a new B-Scan is acquired at the current location and the process is continued. The threshold could be set for all imaging modes or could be set differently depending on the application that the data is being used for. The system may also provide a display in real time of the averaged image as new scans are being collected and averaged. The user could then indicate when the image reaches a desirable quality for their specific analysis purposes and stop the acquisition using a user input device such as a mouse click, touchscreen button, or hardware button.

The main constraint on the quality metric calculation is that it should be made in real time to drive the acquisition. This could be achieved with algorithmic optimization as well as taking advantage of hardware optimizations such as running on specialized circuits such as field programmable gate arrays (FPGAs) or graphic processing units (GPUs) rather than a central processor.

The other time consuming aspect is the registration of successive B-Scans. This can be sped up by always registering the new B-Scan to the speckle reduced image directly. As the acquisition systems become faster, the amount of distortion in the B-Scans reduces, allowing lower degrees of freedom in the registration and hence speeding up the registration process.

In an alternative embodiment, the optimal number of B-scans can also be determined from a non-tracked system using essentially the same principle, in combination with a real time registration of acquired scans, and a real time calculation and examination of the quality metric. In the non-tracked case, the imaging system is not assisting the process by compensating for the patient eye motion, leading to an increased chance that there will be some acquisition epochs where the B-frames will be structurally different from an initial reference. This inadvertently would make the registration performance variable per B-scan pair. Hence in the absence of tracking, it may take more averages (hence a larger scan time) to arrive at the same image quality metric as with the tracked system. In a variation of this alternative embodiment, extra logic can be built into this method which also checks if subsequent scans change the metric of choice in the direction of improvement, and reject all scans which it deems counterproductive to the cause. This will ensure a consistent improvement of image quality, albeit at the cost of some additional acquisition time.

Automated Fundus Image Guided OCT Scanning

Current OCT systems rely on the operator to place the scan at the region or regions of interest. This procedure is not very accurate and it is possible that the operator might miss some region of the tissue that is of interest. Also, the fixed field of view of the OCT scans might miss parts of larger regions of interest. However, there is no way to select a field of view that will work in all cases. A further embodiment of the present invention describes methods for automatically finding regions of interest based on analysis of a fundus image collected from a second imaging modality that is capable of generating an image of the fundus of the eye and to adaptively change the characteristics of the OCT scan based on the detected information.

A variety of adjunct imaging modalities such as fundus cameras, scanning laser ophthalmoscope, line scanning ophthalmoscopes, confocal scanning laser ophthalmoscopes, are known to be combined with OCT systems to provide a view of the fundus for use in alignment or tracking of the OCT device. (See for example U.S. Pat. No. 5,537,162, US Patent Publication No. 2007/0291277, US Patent Publication No. 2012/0249956 hereby incorporated by reference). The main idea of this aspect of the present invention is to automatically find pertinent information based on the fundus imaging system and then direct the OCT to do intelligent scanning based on the information.

Figure 3:
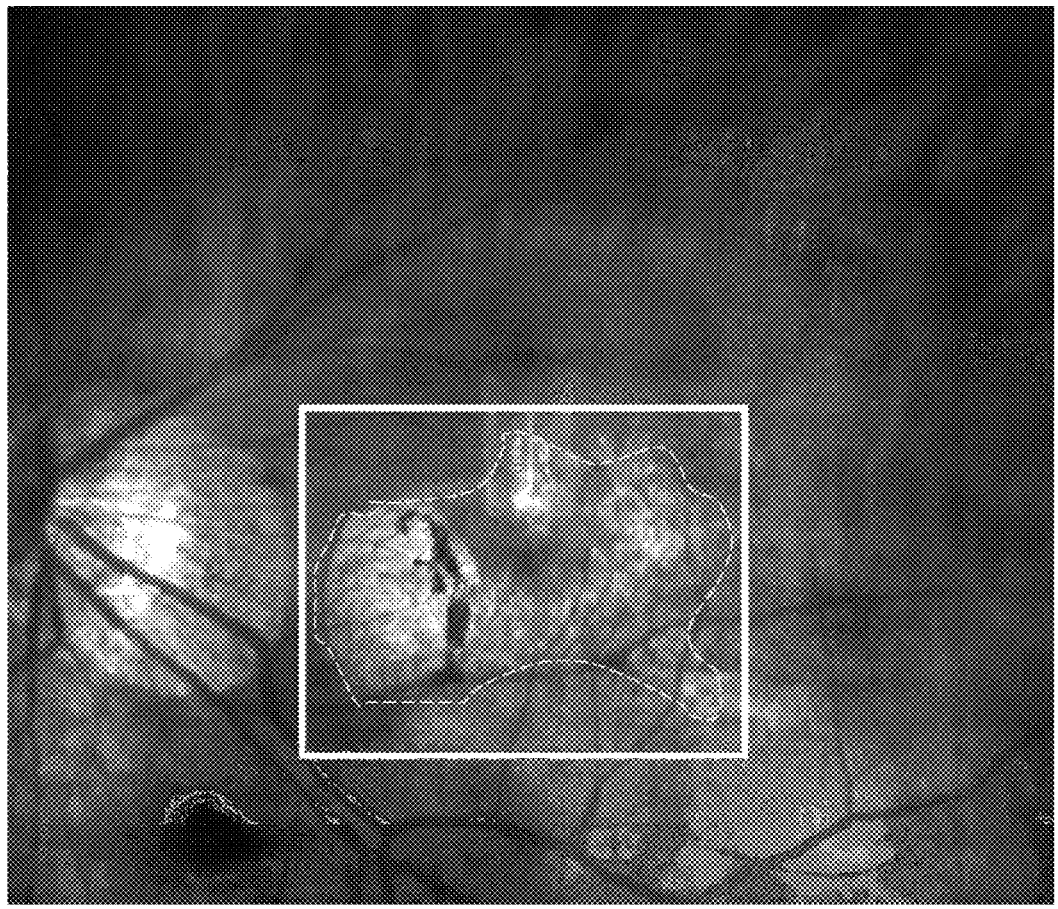
FIG. 3 shows a fundus image that could be used for an embodiment of the present invention directed towards automating collection of OCT image data based on landmarks or abnormalities identified within the fundus image.

In one embodiment of this invention, first a scan of a large field of view of the fundus is obtained using the fundus imaging system. An example of such a fundus image is shown in FIG. 3. Automated image analysis algorithms are then run on the fundus image to find regions of interest. These regions of interest could be normal structures such as the fovea or the optic disk. It could also be pathological regions such as drusen or geographic atrophy (GA) areas. Fast automated analysis of the fundus image enables the accurate localization of the regions of interest like the ones indicated by the region enclosed by the dashed line in FIG. 3. The OCT scan is then acquired in this region of interest as indicated by the rectangular box in FIG. 3. Automated analysis of the fundus image for finding the region of interest might include feature extraction such as blood vessel segmentation, optic disc segmentation, and fovea segmentation. Pathological regions might be extracted based on intensity analysis and/or texture analysis (see for example Iyer et al. "Robust detection and classification of longitudinal changes in color retinal fundus images for monitoring diabetic retinopathy." *Biomedical Engineering, IEEE Transactions on* 53.6 (2006): 1084-1098 and Iyer et al. "Integrated analysis of vascular and nonvascular changes from color retinal fundus image sequences." *Biomedical Engineering, IEEE Transactions on* 54.8 (2007): 1436-1445 hereby incorporated by reference). The expected locations of certain lesions might be initialized by the segmentation of the anatomical features such as the optic disc and fovea. For example, GA usually occurs around the foveal region and peri-papillary atrophy occurs around the optic disc. This system that uses an alternate modality image to locate the regions of interest has the advantage that it can precisely locate features of interest even in pathologic cases. For example in cases where the fovea is severely disrupted due to edema, it might be difficult even to pinpoint the location of the fovea looking at the OCT data. However, using the information of the blood vessel arcades and the optic disk in the fundus image, it will be possible to locate the fovea accurately and then place the scan over that region. The system could also detect multiple regions of interest for the same eye and guide the acquisition of multiple OCT datasets from these regions.

In another embodiment, it will be possible to change the field of view of the OCT image and possibly also the lateral resolution of the OCT image based on the extent of the region of interest that is detected. For example, if a large GA is detected from the fundus image, then it will be possible for the system to automatically change the field of view of the OCT image so that it captures the whole region of the GA. The lateral or transverse (x,y) resolution of the OCT image could be adaptively changed based on a tradeoff between the field of view and the length of time desired for the scan. Another possibility is to change the OCT resolution adaptively around regions of interest. For example for a foveal scan, the highest resolution is desired near the fovea while the scan can be more sparsely sampled towards the periphery. Using the information from the fundus image, the OCT scan resolution can be changed adaptively.

In another embodiment, the region of interest could be selected based on a change detection of the fundus images. In current systems once an OCT scan is obtained, a "repeat scan" is usually placed at the exact same region as the old scan. However in cases where interesting changes are occurring at other places, the current invention will help to draw the clinician's attention to the interesting changes even though the OCT data from the previous visit was not acquired in that region.

In another embodiment, a low resolution wide field OCT "spotter" scan is acquired and stored for each acquisition session of a patient. The spotter scans can be analyzed automatically to find features of interest—for example the retinal thickness at each point. The "spotter" scan from a subsequent session can be compared to the spotter scan from the previous session to quickly find regions of gross change. The OCT system can then be directed to acquire high resolution images over these regions of interest based on the registration between the OCT image and the fundus image guaranteed by the tracking system.

MEGA Scan Patterns

Currently, commercially available OCT systems provide a variety of scan patterns for users to choose from. For example macular scans centered on the macula and optic disc scans centered on the optic disc can be selected depending on clinical information desired. Each type of scan pattern will only support a particular subset of analysis capabilities like retinal nerve fiber layer (RNFL) segmentation or inner limiting membrane-retinal pigment epithelium (ILM-RPE) segmentation. There are also options for obtaining high definition B-scans or line scans with speckle averaging as described earlier in this document. The user usually has to manually select each scan type and then place the scans at the location of interest. Because of the need for acquiring different scan types separately, there is considerable amount of time spent by the users in acquiring the OCT data of interest. The current invention aims to automate much of this and help to avoid the user having to manually select and acquire different scan types.

The speckle reduced tomograms or B-scans allow the doctor to see the layers, morphology, and disruptions in detail with reduced noise and enhanced contrast, while the cube scans allow algorithms to act in three dimensions. There is also the possibility of registering the 2D scans to the 3D scan, where the doctor can see the 2D picture in the context of where particular layers are, or the doctor can focus on areas of interest identified in algorithms acting on the 3D data. There is also the possibility of using the 2D scans with better signal and reduced noise to inform analysis on the cube.

An embodiment of the present invention introduces a new scan pattern for OCT devices with a wider field of view cube, extensive analysis capabilities, variable number of embedded HD scans and automatic HD line placement based on automatic analysis of multiple information sources. The main use of the new scan pattern will be with newer higher speed and/or tracking enabled OCT systems in which significant cubes of data can be acquired without the negative impacts of motion. The scan pattern could be the "one" and only scan pattern that is needed and will provide quantitative and qualitative information about the macula, optic disc and other pathologies of interest.

The main components of a preferred embodiment of the new Mega Scan pattern are the following:

1. A wide field OCT cube scan with a minimum field of view of 12 mm×12 mm that contains both the macular and optic disc regions
2. Automatically generated analysis including but not limited to:
   a. ILM-RPE segmentation
   b. RNFL Segmentation
   c. Ganglion cell complex (GCC) Segmentation
   d. Other retinal layer segmentation
   e. Optic disc detection
   f. Optic Nerve Head segmentation
   g. Fovea detection
   h. Automatic ETDRS grid placement and retinal thickness measurements
   i. Automatic extraction of RNFL thickness around the optic disc
3. High Definition (HD) Line Scans with speckle averaging embedded in the cube. The number of HD scans can be fixed or variable based on automatically identified parameters.
4. The location of the HD scan placement is automatically determined based on
   a. Segmentation of Regions of Interest from SLO/LSO image
   b. Segmentation of Regions of interest from OCT scout scans (very low resolution cube scan at the beginning)

Scan Patterns for Imaging Retinas with Large Axial Depth Range

Frequency domain OCT provides images of finite depth range, where to achieve deeper imaging range one must sample the spectra with higher resolution. Although in swept source OCT one has the option to sample the spectra faster, or slow down the sweep rate of the laser (see for example U.S. patent application Ser. No. 13/354,066 filed Jan. 19, 2012) it is still advantageous, in order to achieve a maximum scanning rate, to limit the required axial imaging range. Some structures of interest, for example the human retina, have a relatively thin section of interest near a curved surface that itself exists at a wide variety of depths over the lateral field of view. It is therefore useful in such tissues to be able to image over a variable region of interest in depth over the field of view imaged in a single volume. In this case the volume imaged is not a simple cube bounded by the lateral extent of the field of view and the maximum and minimum depth, but a relatively smaller volume that exists at a location that is a small depth away from a surface. This has the potential to maximize scanning speed and minimize unnecessary data processing and storage. It is an aspect of the present invention to allow a system to scan a wide retina field on virtually any patient without the need of extreme depth range capability. The instrument could be designed with specific scans for high myopes or could make scan adjustments based on automated processing of some initial data that characterizes the degree of myopia present in a particular eye.

In time domain OCT, it is conceptually possible to vary the interferometer delay length in response to an observed depth change in the tissue. In early frequency domain systems, the problem was commonly observed as an undesirable tilt or curvature to the image, which made it difficult or impossible to image the desired lateral field of view without parts of the retina going beyond the top or bottom of the image space and causing distracting aliasing artifacts. By montaging several small fields of view, and adjusting the delay line in between fields, a wider field could usually be obtained but at a significant effort. If the problem was a simple tilt of the interesting surface, and the tilt was fortunate enough to lie primarily in the slow scan direction of the volume scan, the axial depth tracking algorithms implemented by some systems would potentially cancel the depth drift that could occur through the volume.

Here, optical coherence tomography scan patterns optimized for collecting volume scans of retinas with large variation in axial depth are disclosed. In these patterns the fast scanning direction is approximately parallel to a contour of constant axial depth whereas the approximately perpendicular slow scan direction corresponds to a direction of large magnitude depth change. The change in depth in the slow scanning direction is orders of magnitude slower than the change in the fast direction and can be compensated by adjustment of the reference arm during scanning. Composite montaged scans consisting of multiple areas of dissimilar scan patterns are also described. This type of scan pattern is particularly useful for scanning high myope patients off of the optical axis, but it may be useful for all types of patients for ultrawide field OCT. The patterns could be initially implemented for nerve head scanning of high myope patients by rotating the scan pattern such that the fast scan is in the vertical direction instead of the horizontal direction as is most common now, in combination with an axial tracking mechanism.

The geometry of the eye causes an apparent axial shift of the tissue as the scan progresses outward in field angle toward the anterior eye, which becomes more severe in myopic eyes. Mitigating scan strategies are discussed. One scan strategy that allows for maximum scan speed with the greatest consistency between eyes of different type includes circular or arcuate scans which maintain a relatively constant depth across a fast b-scan, while allowing the reference arm to adjusts as the slow scan direction moves across contours of changing depth.

Figure 4:
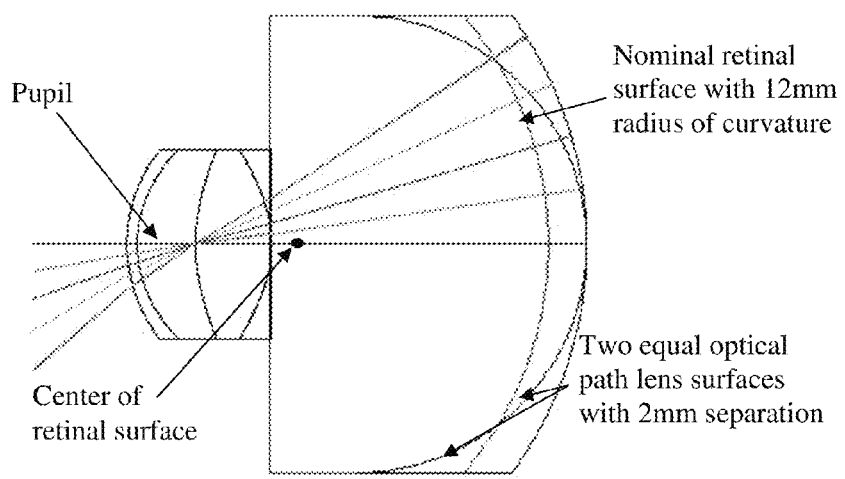
FIG. 4 shows a Humphrey eye model having a retinal surface with nominal 12 mm radius of curvature with four rays correspond to 10°, 20°, 30° and 40° view angles.

FIG. 4 shows a simple geometrical model of the eye with a nominal reference surface with 12 mm radius of curvature. Four rays corresponding to 10°, 20°, 30° and 40° view angles are shown. Fundamentally, because the scanner is imaged to the entrance pupil of the eye, all scan angles have the same path length at the pupil. From there it is easy to see that the center from which optical beams propagate in the eye is not the same as the geometrical center of the retina. The model can be extended to consider 'average' variations in eyes with change in refractive error.

Myopic eyes are described by Atchison, D. A. et al. in "Eye Shape in Emmetropia and Myopia" *IOVS* 45, 3380-3386 (2004). According to Atchison et al., "with an increase in myopic refractive correction, myopic eyes became much larger in all three dimensions, but more so in length (0.35 mm/D, 95% confidence interval [CI] 0.28-0.40) than in height (0.19 mm/D, 95% CI 0.09-0.29) and more so in height than in width (0.10 mm/D, 95% CI 0.01-0.20). Based on height and length dimensions, 25% and 29% of myopic eyes exclusively fitted global expansion and axial elongation models, respectively. Based on width and length dimensions, 17% and 39% of myopic eyes exclusively fitted the global expansion and axial elongation models, respectively.

Figures 5, 6:
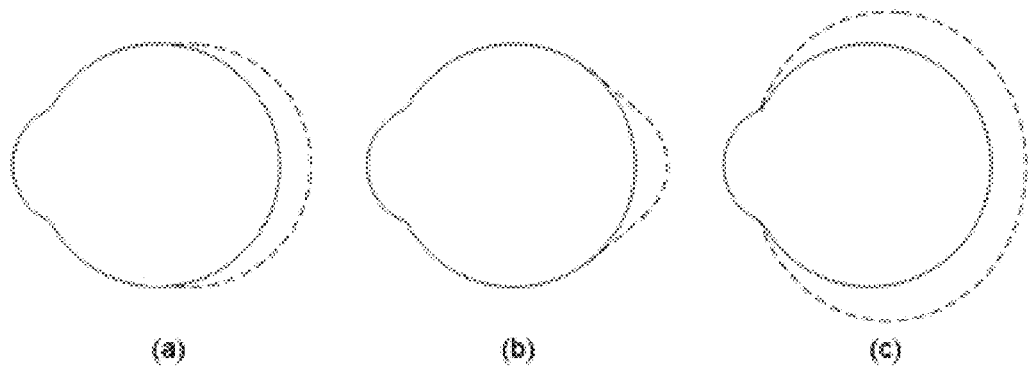
FIG. 5 illustrates three different models that can be used to calculate the apparent depth changes due to myopia in the eye of a patient.
FIG. 6 shows a table summarizing modeling results for optical path length to the retina at a range of scan angles for an emmetropic (normal) eye and a highly myopic eye (−24D).

FIG. 5 illustrates three models for how myopia can manifest itself in the eye. FIG. 5(*a*) illustrates equatorial stretching, FIG. 5(*b*) illustrates posterior pole elongation, and FIG. 5(*c*) illustrates global expansion. These models can be used to calculate optical path length differences for various angles based on the degree of myopia present. Any simple eye model can be used to calculate path length differences with minimal error.

FIG. 6 shows a table summarizing modeling results for optical path length to the retina at a range of scan angles for an emmetropic (normal) eye and a highly myopic eye (−24D). The expected depth (in mm) of a portion of retina at a particular field angle is described relative to the depth on axis. Both models show that the axial distance difference increases with field angle. The amount of axial difference with field increases with myopia. The amount of depth variation in high myopes is very significant with respect to the thickness of the retina even at small field angles, whereas a relatively large field angle must be subtended for the difference to be significant in normal eyes.

Experimental observations using a typical size scan, +/−10 degrees scan (6 mm), on the Cirrus HD-OCT instrument on extreme or 'high myopes' indicates a need for increased image depth in OCT. The problem is typical for imaging optic nerve head (located approximately 15 degrees from the optic axis of the eye) in high myopes, and is sometimes observed in the macula of high myopes with staphyloma (pathological posterior pole stretching).

Several scan configurations are proposed to meet the imaging depths required for high myopes over normal field angles, or normal eyes over extremely wide field angles. The first strategy includes increasing the overall system imaging range. This approach was described in U.S. patent application Ser. No. 13/354,066 filed Jan. 19, 2012. In general the cost of increasing the range is to decrease the speed of acquisition by a proportional amount (e.g. to double the image range requires speed reduction by a factor of 2). A large scanning depth may be useful in a preview mode in order to estimate the amount of depth variation present over the field of view of the scan, which may be used by the system to choose a scanning strategy or determine parameters to use in the scanning strategy.

Figure 7A:
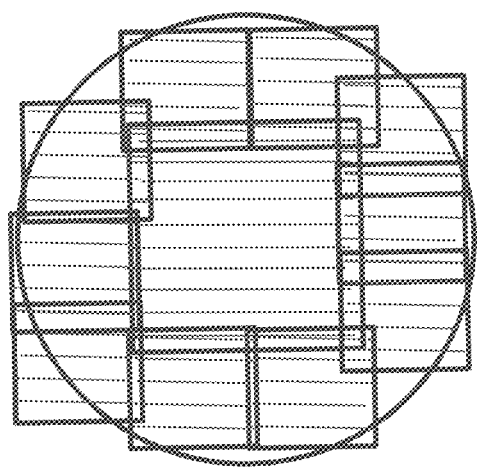
In FIG. 7a a tiled scan pattern is used with all tiles having constant or near constant depth. Smaller area tiles are used as the radius of curvature increases.

The second strategy include maintaining a minimum image range, but tiling regions and adjusting a z position between individual images or tiles as is illustrated in FIG. 7. The tiling strategy employs a series of constant depth scans over the transverse extent of the eye with an increasing number of smaller tiles required for greater radial angle because of the increasing rate of depth change with transverse position at these locations. The maximum size of the tiles depends on the refractive error. Some amount of tile overlap is required to register the frames, although additional information from a tracking system can minimize this need. As the number of tiles increases, the amount of time devoted to the overlapped regions becomes significant.

A third and preferred option includes acquisition of data while allowing a z-tracking algorithm to adjust the reference arm slowly though the duration of the acquisition. Such a z-tracking system is described in U.S. Patent Publication No. 2012/0249956 hereby incorporated by reference. This approach takes advantage of the idea that the retina varies in depth less over a small region than over a large region, and with appropriate scan geometry, the required velocity of the reference arm and feedback mechanism is greatly reduced. This approach works best when the fast scan direction is approximately circumferential with respect to axis of eye (and therefore introducing no tilt) while the slow scan is radial. Scan patterns may be designed which are theoretically perfect in this regard. With zero tilt relative to a perfectly spherical eye, this would be a circle scan. Each B-scan is taken in an arc with its center at the portion of the retina with the largest apparent depth described as the optical axis (centered at the fovea in a normal eye). When the scan pattern is displaced from the deepest portion of the retina, for example to image the optic nerve head, or an off-axis pathology, each arcuate B-scan maintains its center near the deepest portion of the retina, however this center is no longer at the center of the scan pattern. It is desirable to avoid circle scans of less than a minimum radius in order that a simple safety circuit can easily monitor that the scanning mechanism is actively scanning through an angle larger than a predetermined minimum established by a safety analysis; therefore one may include a rectangular scan, radial scan, or other scan for regions near the axis.

Figure 7B:
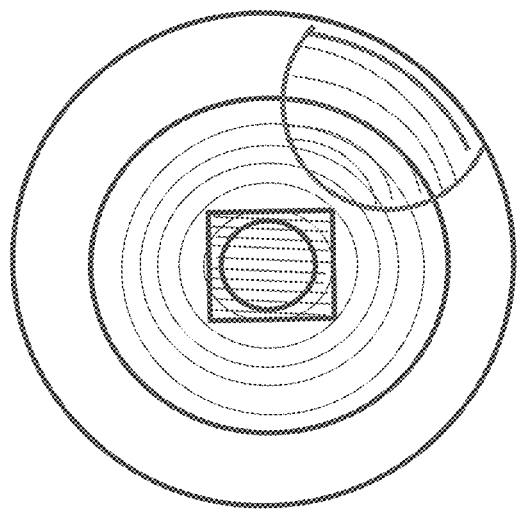
In FIG. 7b a series of scans of varying geometries is optimized to minimize depth change in the fast scan direction, allowing a slow z correction.

FIG. 7b illustrates a series of scans optimized to minimize depth change in the fast scan direction, allowing a slow z correction. A composite scan is illustrated consisting of: 1) a non-circumferential scan for the small area near the eye axis as required by safely limitations, 2) a circular scan centered on the axis of the eye covering the instantaneous field of view of the optical system, and 3) an arcuate scan displaced from the axis of the eye, however the arcs of each b-scan is centered on the axis of the eye. Such an arcuate scan may be useful for taking a subfield at high definition, or taking an image after tip-tilting the acquisition unit away from the axis of the eye.

Figure 8:
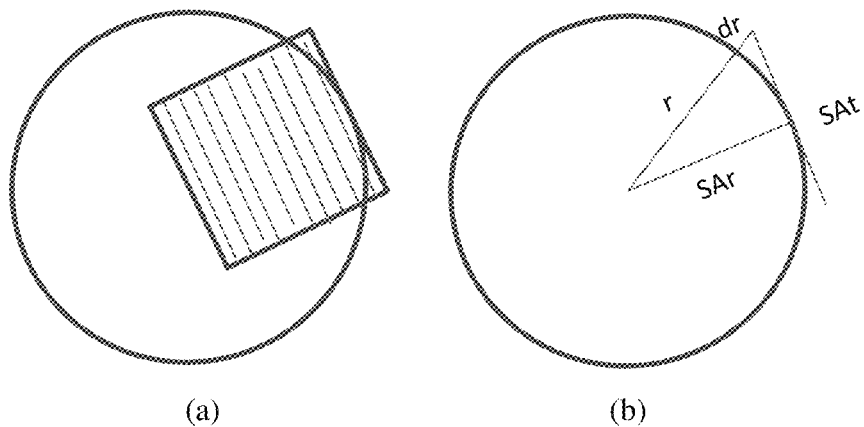
FIG. 8a shows fast scan lines oriented tangentially to the eye axis.
FIG. 8b shows the radial component, dr, of a tangential B-scan of length SAt, located at radial angle, SAr.

For a rectangular scan, the approximation to circumferential scanning can become better when scanning far from the axis. This is fortunate because the change in axial distance with respect to radial angle also increases far from the axis as illustrated in FIG. 8. FIG. 8a shows fast scan lines oriented tangentially to the eye axis. FIG. 8b shows the radial component, dr, of a tangential B-scan of length SAt, located at radial distance, SAr. The radial component of the rectangular scan oriented to minimize the radial component in the fast scan can be approximated using the Pythagorean theorem according to:

$$dr = sqrt(SAr^2 + (SAt/2)^2) - SAr.$$

One can estimate that the radial component of a tangentially oriented +/−20 scan at 60 degrees from the axis is approximately 3 degrees. Modeling of the depth required for a 3 degree radial change at −60 degrees indicates that it will be very close to consuming a full 4 mm image with the apparent retinal tilt. Reducing the length of the tangential scan improves the approximation to the arcuate scan. A tangentially oriented rectangular scan of +/−11 degrees achieves a radial component of 1 degree at the extreme field, which is sufficient to avoid problems with depth range in a normal eye.

Note that multiple volumes may be acquired with overlapping regions and that acquisition may occur at different a-scan angles. Such volumes may be used for volume registration to remove artifacts. In the case of staphyloma, where the center staphyloma does not correspond with the fovea, the above methods may be used, however the center of the scan pattern should be centered on the perceived deepest point of the staphyloma to define the axis of the eye, rather than on the fovea.

Although various applications and embodiments that incorporate the teachings of the present invention have been shown and described in detail herein, those skilled in the art can readily devise other varied embodiments that still incorporate these teachings.

The following references are hereby incorporated by reference:

Patent Documents

U.S. Pat. No. 5,321,501
U.S. Pat. No. 5,537,162
U.S. Pat. No. 7,301,644
U.S. Pat. No. 7,884,945
US Patent Publication No. 2007/0291277
US Patent Publication No. 2012/0249956
U.S. patent application Ser. No. 13/354,066

Non-Patent Literature

Huang et al. "Optical Coherence Tomography" Science 254 (5035):1178 1991.
Nassif et al. "In vivo human retinal imaging by ultrahigh-speed spectral domain optical coherence tomography" Optics Letters 29(5):480 2004.
Choma, M. A., et al. "Sensitivity advantage of swept source and Fourier domain optical coherence tomography" Optics Express 11(18): 2183 2003.
Wojtkowski, et al., "Three-dimensional retinal imaging with high-speed ultrahigh-resolution optical coherence tomography," *Ophthalmology* 112(10):1734 2005.
Lee et al. "In vivo optical frequency domain imaging of human retina and choroid," *Optics Express* 14(10):4403 2006.
Leitgeb et al. "Ultrahigh resolution Fourier domain optical coherence tomography," Optics Express 12(10):2156 (2004).
Atchison, D. A. et al. Eye Shape in Emmetropia and Myopia. *IOVS* 45, 3380-3386 (2004).
Iyer et al. "Robust detection and classification of longitudinal changes in color retinal fundus images for monitoring diabetic retinopathy." *Biomedical Engineering, IEEE Transactions on* 53.6 (2006): 1084-1098.
Iyer et al. "Integrated analysis of vascular and nonvascular changes from color retinal fundus image sequences." *Biomedical Engineering, IEEE Transactions on* 54.8 (2007): 1436-1445.

What is claimed is:

1. A method of collecting optical coherence tomography (OCT) image data of an eye of a patient, said method comprising:
   collecting two or more OCT scans, wherein each scan is made over a series of transverse location on the eye of a patient;
   averaging the two or more scans to create an averaged scan;
   determining a quality metric for the averaged scan;
   comparing the quality metric to a predefined value to determine whether additional OCT scans should be collected; and
   collecting one or more additional scans, adding the additional scans to the average and determining a quality metric until the determined quality metric exceeds a predefined value.

2. A method as recited in claim 1, wherein the scans are B-scans.

3. A method as recited in claim 2 wherein the B-scans that are averaged are collected from the same transverse location on the eye.

4. A method as recited in claim 2 wherein the B-scans are registered prior to determining the quality metric.

5. A method as recited in claim 1, wherein the predefined value depends on the location or pathology of interest.

6. A method as recited in claim 5, wherein the quality metric is based on overall intensity characteristics of the averaged image.

7. A method as recited in claim 5, wherein the quality metric is based on a particular layer or region.

8. A method of collecting optical coherence tomography (OCT) image data of an eye of a patient, said method comprising:
   (a) collecting a first plurality of OCT scans, wherein each scan is made over a series of transverse location on the eye of a patient;
   (b) averaging the first plurality of scans to create an averaged scan;
   (c) determining a initial quality metric for the averaged scan;
   (d) collecting an additional scan, adding the additional scan to the average and determining an updated quality metric;
   (e) comparing the initial and updated quality metrics and if the difference between the quality metrics exceeds a predefined value, repeating steps (d) and (e) until the difference between the most recently determined quality metric and the immediately preceding quality metric is less than the predefined value.

9. A method as recited in claim 8, wherein the scans are B-scans.

10. A method as recited in claim 9 wherein the B-scans that are averaged are collected from the same transverse location on the eye.

11. A method as recited in claim 9 wherein the B-scans are registered prior to determining the quality metric.

12. A method as recited in claim 8, wherein the predefined value depends on the location or pathology of interest.

13. A method as recited in claim 12, wherein the quality metric is based on overall intensity characteristics of the averaged image.

14. A method as recited in claim 12, wherein the quality metric is based on a particular layer or region.

15. An optical coherence tomography (OCT) system for collecting data from the eye of a patient, the system comprising:
   a light source for generating a light beam propagating along an axis;
   a beam divider for directing a first portion of the light beam into a reference arm and a second portion of the light beam into a sample arm;
   optics for scanning the light beam in the sample arm over the eye of a patient to a plurality of positions in a plane perpendicular to the propagation axis of the beam to create a plurality of B-scans;
   a detector for measuring light radiation returning from the sample and reference arms and generating output signals in response thereto; and
   a processor for averaging two or more B-scans and determining a quality metric for the averaged B-scans, comparing the quality metric to a predefined value to determine if additional data should be collected, and for sending a signal to stop acquisition of data should the metric exceed the predefined value.

16. A method of collecting optical coherence tomography (OCT) data of an eye of a patient, said method comprising:
   collecting a 3D volume of data over a range of transverse locations on the eye of the patient;
   collecting one or more high definition B-scans at a subset of the transverse locations covered in the 3D volume, wherein each high definition B-scan comprises a plurality of individual B-scans collected at substantially the same transverse location and averaged together, and wherein the locations of the high definition B-scans are determined automatically based on areas of interest with the eye;
   performing a multiplicity of analyses on the 3D volume and high definition B-scans; and
   displaying one or more images and analysis results.

17. A method as recited in claim 16, wherein the analyses are selected from the list including: ILM-RPE segmentation, RNFL Segmentation, Ganglion cell complex (GCC) Segmentation, Other retinal layer segmentation, Optic disc detection, Optic Nerve Head segmentation, Fovea detection, Automatic ETDRS grid placement and retinal thickness measurements, and Automatic extraction of RNFL thickness around the optic disc.

18. A method as recited in claim 17, wherein the 3D volume covers a minimum field of view of 12×12 mm and encompasses both the macula and optic disc.

19. A method as recited in claim 17, wherein the one or more high definition B-scans locations are determined using information from a fundus image generated by a separate fundus imaging modality.

20. A method as recited in claim 17 wherein the high definition B-scans locations are determined using information from OCT data.

* * * * *